United States Patent [19]

Henderson et al.

[11] Patent Number: 4,928,696
[45] Date of Patent: May 29, 1990

[54] ELECTRODE-SUPPORTING HEADSET

[75] Inventors: Don J. Henderson, Danville; Robert Brady, Pescadero; Foster R. Gamble, Woodside; James V. Hardt, San Francisco; Howard Friedfeld, Palo Alto; Don Salerno, Mountain View; Tad Swanson, Menlo Park; Maureen R. Sansing, Oakland, all of Calif.

[73] Assignee: MindCenter Corporation, Palo Alto, Calif.

[21] Appl. No.: 385,595

[22] Filed: Jul. 26, 1989

[51] Int. Cl.$^5$ ................................................ A61B 5/04
[52] U.S. Cl. ..................................... 128/644; 128/791
[58] Field of Search ............... 128/89 A, 97.1, 380, 128/791, 639, 644, 731, 802

[56] References Cited

U.S. PATENT DOCUMENTS

| 1,849,745 | 3/1932 | Hoffman | 128/791 |
| 2,842,136 | 7/1958 | Browner | 128/791 |
| 3,998,213 | 12/1976 | Price | 128/644 |

FOREIGN PATENT DOCUMENTS 0199214 10/1986 European Pat. Off. ............ 128/644

Primary Examiner—Lee S. Cohen
Assistant Examiner—Scott Getzow
Attorney, Agent, or Firm—Townsend and Townsend

[57] ABSTRACT

A headset is provided for holding electrodes against a subject's head for extended periods of time which has several pairs of support poles or rods whereon several flexible electrode supporting bands attach that allow variable placement and holding of various electrodes in various regions on the head. The regions for placement are the occipital, the central and the frontal regions of the head. The electrode supporting bands are elastic and are attached by hook and eye means to opposing rods so that the bands can be slidably and flexibly adjustably mounted on the headset apparatus. This allows tension holding the electrodes against the subject's head to be adjusted for an optimum balance of comfort and contact.

9 Claims, 1 Drawing Sheet

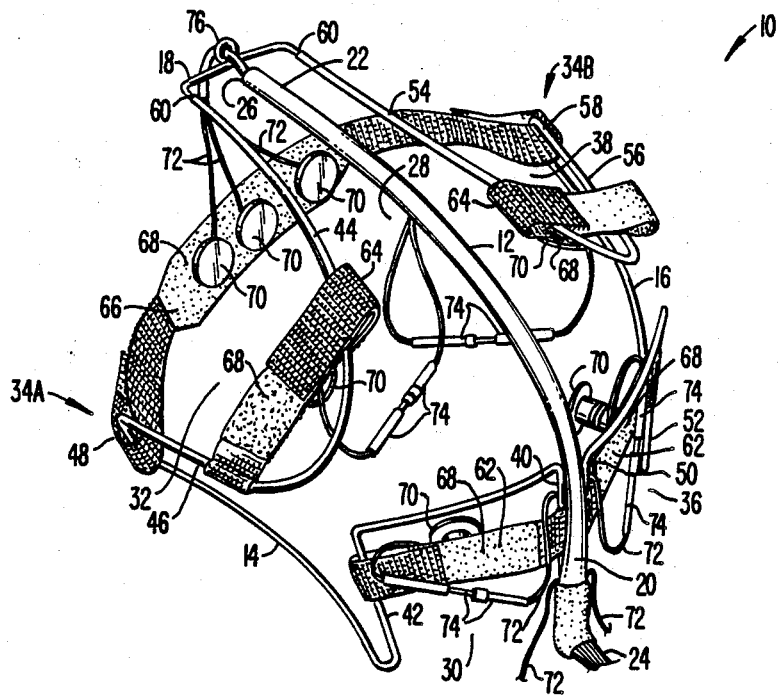
FIG._1.

ELECTRODE-SUPPORTING HEADSET

BACKGROUND OF THE INVENTION

This invention relates to an electrode supporting headset apparatus in general, and more specifically, to an electrode supporting headset apparatus that is functionally adjustable and light weight for repeated and long term use in monitoring a subject's electrical signals from the head during electroencephalography and electromycephalography.

Electroencephalography (EEG) and electromycephalography (EMG) are clinical methods for monitoring multiple channels of human electrical signal waves. Part of this process requires preparing the skin and individually attaching electrodes to the scalp in predetermined areas that are well known in the art for monitoring the subject's brain waves. More recently, the personal use of EEG and EMG biofeedback information for fostering learning EEG self-control and increasing well-being has further increased the use of EEG and EMG monitoring devices.

The greatest problem with most EEG and EMG monitoring systems is the actual placement and securing of the individual electrodes to the subject's scalp. Several individual electrodes must be located and specifically placed on a subject's scalp with good electrical contact established between the electrode and the subject's scalp. The current practice utilizes highly conductive, miniature, "cup" shaped electrodes which are fastened to the subject's scalp by means of an adhesive-type electrically conductive paste or cream. The approach for locating and placing electrodes on a subject's scalp has long been a trial and error method.

Exact placement of the various electrodes has long been a cumbersome, messy and time consuming endeavor. The time required is generally 30 to 45 minutes. In repetitive testing and monitoring, locating electrodes in the exact same position as before can be difficult and highly unlikely. Moreover, the chances of obtaining and maintaining good electrical contact with the scalp at all various locations can prove difficult due to the differences in skull size and shape and the amount and texture of the hair of the different subjects.

The more recent method of using a helmet-like apparatus to hold electrodes in place also has drawbacks. For example, U.S. Pat. No. 4,683,892 to Johnsson, et al. discloses a helmet of a type used in the past to mount electrodes. It comprises a solid shell cover within which electrodes are disposed for mounting to the scalp. It is subject to many of the limitations discussed above, as well as other drawbacks. These include irritation from pressure points due to uneven tensions in electrode placement, fatigue and heat due to the cumbersome apparatus worn for extended periods of time, and the purchasing of expensive equipment using sophisticated mechanical means for maintaining electrode contact.

Therefore, what is needed is an electrode supporting headset that is easy to use having electrode placement memory, is light weight with a cool airflow design, and is not expensive to manufacture, purchase or replace.

SUMMARY OF THE INVENTION

According to the invention, a headset is provided for holding electrodes against a subject's head for extended periods of time which has several pairs of support poles or rods whereon several flexible electrode supporting bands attach that allow variable placement and holding of various electrodes in various regions on the head. The regions for placement are the occipital, the central and the frontal regions of the head. The electrode supporting bands are elastic and are attached in a loop by hook and eye pad means to opposing rods so that the bands can be slidably and flexibly adjustably mounted on the headset apparatus. This allows tension holding the electrodes against the subject's head to be adjusted for an optimum balance of comfort and electrical contact. The electrodes also attach to the bands by hook and eye pads, thus allowing easy pinpoint placement during use, and detachability for sterilization for reuse or for replacement.

As the tension in the bands is adjusted and the electrodes are placed, they are held in the most optimal position. The apparatus allows the electrodes to be removed at the end of the monitoring session for easy repositioning for the next session. Since the electrodes are held in their optimal position from the last use, time is saved during repositioning since the optimal positions need not be relocated. Moreover, instead of attaching the electrodes with a thick, sticky adhesive paste, all that is needed for contact between the skin of the subject and the electrodes is a modest quantity of an electrolytic gel that increases conductivity. It can be used sparingly since it is not required to be used as an adhesive means for keeping the electrodes attached to the scalp. Furthermore, this saves time and money by reducing the cleanup mess for both the operator and the subject.

The invention will be better understood by reference to the following detailed description in connection with the attached drawings.

BRIEF DESCRIPTION OF THE DRAWINGS

FIG. 1 is a rear perspective view of one embodiment of a headset of the present invention.

DETAILED DESCRIPTION OF THE SPECIFIC EMBODIMENTS

In FIG. 1, headset 10 comprises a tubular support member 12, a first tubular mount member 14, a second tubular mount member 16 and U-shaped rod 18.

The tubular support member 12 has a base end 20 and a frontal end 22 wherein the tubular support member 12 is shaped to extend from the base end 20 to the frontal end 22 along a central distal contour of the subject's head. At the base end there is a first opening 24 that extends through tubular support member to a second opening 26 at frontal end 22. Positioned between the base end 20 and the frontal end 22 is a third opening 28 that opens towards the subject's head. Attached to the right occipital side of the support member base end 20 is the first tubular mount member 14. This first tubular mount member 14 has a first suspension segment 30, a second suspension segment 32, and the first half of a third suspension segment 34A. These suspension segments each have two opposing parallel poles that are separated by a space. The first suspension segment 30 is disposed between the right base pole 40, which is attached to base end 20, and a right vertical side pole 42, positioned behind the right ear area. The second suspension segment 32 is disposed between the right central pole 44, above the right central area, and the right horizontal pole 46, above the right ear area. Finally, the first half of the third suspension segment 34A is disposed at a right forward position and includes right temple pole 48.

The second tubular mount member 16 is rigidly attached to the left occipital side of the base end 20. This second tubular mount member 16 includes the fourth suspension segment 36, the fifth suspension segment 38 and the second half of the third suspension segment 34B. These suspension segments also comprise opposing parallel poles separated by a space. The fourth suspension segment 36 is disposed between the left base pole 50 attached to base end 20 and the left vertical side pole 52 behind the left ear region. The fifth suspension segment 38 is disposed between the left central pole 54, above the left central area, and the left horizontal pole 56 above the right ear area. And lastly, the second half of the third suspension segment 34B is disposed at the left forward position and includes left temple pole 58.

Each tubular mount member 14 and 16 is constructed of a rod bent along a path to form the various suspension segments. It will be apparent to one skilled in the art that other ways of forming each tubular mount member that will include the various suspension segments are possible; therefore, this description is not intended to limit the full scope of the inventor's invention. The headset 10 is asymmetrical, meaning that the left side is a mirror-image of the right. One end of the rod attaches to the base end 20 of the tubular support member 12. The first suspension segment 30 is formed as the rod extends first vertically upward above the occipital region. The rod then bends away from the support member 12 following horizontally above the top occipital region until past the outside occipital region. The rod extends downward for a second vertical length and forms an inverted U, thus completing the first (fourth) suspension segment 30 (36).

The second vertical section extends a length approximately equal to the first vertical length. At the bottom, it curves relatively sharply 180° to extend vertically behind the ear position. The rod curves forward along the ear area before extending horizontally above the ear until reaching the temple area. The rod then extends vertically upwards a short length until it bends horizontally back below the central area of the head. This completed portion is square-C-shaped and forms one of the third suspension segment halves 34A and 34B. The rod extends back below the central area horizontally past the ear area before curving upward and forward towards the top of the head and the frontal area where it extends horizontally before ending near the top of the forehead. This section partially circles the central area above and below. It is the rod portions above and below the central area that form the second (fifth) suspension segments 32 (38).

Each frontal end of the mount members 14 and 16 has a mount member opening 60 extending axially internal the mount member 14 and 16. The U-shaped rod 18 telescopically inserts a prong into each the first and the second mount member 14 and 16. The U-shaped rod 18 maintains a separation between the first and the second tubular mount member 14 and 16, and can be replaced with a U-shaped rod (not shown) of a different width for selection in accordance with variations in head size. The U-shaped rod 18 also telescopically adjusts for finer size adjustment.

The headset 10 further comprises a set of flexible electrode supporting bands for holding a set of electrodes against the subject's head. The supporting bands include an occipital pair 62, a central pair 64 and a frontal band 66. Each band is made of an elastic ribbon strap as commonly used material that has tube portions at each end for slidably attaching on the opposing pairs of poles, or suspension segments. The tube portions can be formed by any means such as, but not limited to, sewing or attaching one end back on itself by using hook and eye means. Hook and eye means 68 is the preferred method for mounting since it allows adjusting the length of the bands for adjusting the pressure between the band and the head while holding the electrodes in place.

The occipital pair 62 mount one across the first suspension segment 30 and another across the fourth suspension segment 36 for placing electrodes on the occipital region of the head. The central pair 64 attach one across the second suspension segment 32 and the other across the fifth suspension segment 38 for holding electrodes on the central region. The front band 66 mounts across the forehead by attaching one end to the first half of the third suspension segment 34A and the other end to the second half of the third suspension segment 34B. Each electrode 70 has hook and eye means 68 attached on its back side for attaching to the face of the bands abutting the head of the subject and for abutting the metal face of the electrode against the head. Electrical contact is enhanced between the electrodes 70 and the subject's skin by using any suitable electrolyte gel lightly applied to the electrode surface.

Wires 72 run through tubular support member 12 and selectively exit through the support member openings for attaching to each electrode. Each electrode attaches to each wire by an electrode wire receptor contact 74. The wires 72 also extend out the base end 20 of the tubular support member 12 for connecting to an appropriate signal receiving unit (not shown) for processing the signals received through the electrodes. Also, U-shaped rod 18 has an open loop 76 at its base end for either holding the wires 72 or the frontal end 22 of the support member 12 (not shown) or both.

The operation of this headset 10 allows specific placement of the electrodes 70 for the best, most optimal contact on the subject's skin. The hook and eye means 68 allows easy adjustment of the various bands for holding the electrodes in place once optimal contact is made. Furthermore, the U-shaped rod 18 can slide internally in the mount members, or even be changed for a U-shaped rod with a wider width, for universally adapting to a variety of head shapes and sizes. Also, the flexible bands that hold the electrodes allow the electrodes to be of a larger diameter for increasing electrical receptivity and reducing pressure point sensitivity. It can be appreciated from this invention that once all the electrodes are in place, which can take 30 to 40 minutes, the headset allows the electrodes to be removed at the end of the monitoring period for reuse in their previous position without needing 30 minutes for resetting.

The invention has now been explained with reference to specific embodiments. Other embodiments will be apparent to those of ordinary skill in the art in view of this description. It is therefore not intended that this invention be limited, except as indicated by the appended claims.

What is claimed:

1. A headset apparatus for detecting electrical signals from a head of a subject for extended periods comprising:

a tubular support member having a base end and a frontal end, said tubular support member shaped to extend from a base to a forehead of said head along a central distal contour;

a first tubular mount member rigidly attached to a right occipital side of said base end, said first tubular mount member comprising a first suspension segment, a second suspension segment and a first half of a third suspension segment, each said suspension segment comprising opposing parallel pole members separated by a space, said first suspension segment being disposed between said base end and a right vertical side pole member disposed behind a right ear position, said second suspension segment being disposed between said frontal end and a right horizontal pole member above said right ear position, and said first half of said third segment being disposed at a right forward position adjacent a right temple portion;

a second tubular mount member rigidly attached to a left occipital side of said base end, said second tubular mount member comprising a fourth suspension segment, a fifth suspension segment and a second half of said third suspension segment, each said suspension segment comprising opposing parallel pole members separated by a space, said fourth suspension segment being disposed between said base end and a left vertical side pole member disposed behind a left ear position, said fifth suspension segment being disposed between said forward end and a left horizontal pole member above said left ear position, and said second half of said third segment being disposed at a left forward position adjacent a left temple portion; and a plurality of flexible electrode supporting band means, including at least one electrode mounted to each said band means, each of said band means are for pressing said electrodes against said head at occipital, frontal and central portions of said head, each said band means having at each end means for forming a tube slidably attachable on opposing pairs of said pole members and including means for adjusting the length of said band means between said opposing pole member pairs to adjust pressure between the band means and the head.

2. The headset apparatus according to claim 1, wherein said base end of said tubular support member comprises first opening extending the length of said tubular support member; a second opening in said frontal end connecting said first opening; a third opening between said base end and said frontal end; and a plurality of wires disposed in said tubular support member and exiting at said openings and connecting to said electrodes.

3. The headset apparatus according to claim 2, wherein said electrodes demountably attach to at least one of said flexible electrode supporting band means by hook and eye fastener means.

4. The headset apparatus according to claim 2, further comprising an attachment means attaching said electrodes and said wires wherein said attachment means comprises a male-female electrical union joint.

5. The headset apparatus according to claim 1, further including U-shaped rod means attaching a frontal end of said first tubular mount member to a corresponding frontal end of said second tubular mount member for maintaining separation between said first and second tubular mount members.

6. The headset apparatus according to claim 5, further including a wiring harness extending from said tubular support member to at least one of said band means and wherein said U-shaped rod means includes means for suspending said wiring harness.

7. The headset apparatus according to claim 5, wherein said u-shaped rod means is removably telescopically attachable to said frontal end of said first tubular mount member and to said corresponding frontal end of said second tubular mount member whereby spacing between said first tubular mount member and said second tubular mount member can be selected in accordance with variations in head size.

8. The headset apparatus according to claim 1, wherein each said flexible electrode supporting band means demountably attach by hook and eye fastener means.

9. The headset apparatus according to claim 1, wherein said band means comprise an elastic ribbon strap.

* * * * *